US012667549B2

(12) United States Patent
Aramini et al.

(10) Patent No.: US 12,667,549 B2
(45) Date of Patent: Jun. 30, 2026

(54) SYNERGISTIC ADMIXTURES OF GABAPENTIN AND KETOPROFEN, PHARMACEUTICAL COMPOSITIONS AND THEIR MEDICAL USE

(71) Applicant: DOMPÉ FARMACEUTICI S.P.A., Milan (IT)

(72) Inventors: Andrea Aramini, L'Aquila (IT); Marcello Allegretti, Rome (IT); Gianluca Bianchini, L'Aquila (IT); Samuele Lillini, Cardito (IT); Mara Tomassetti, Naples (IT); Laura Brandolini, L'Aquila (IT)

(73) Assignee: DOMPÉ FARMACEUTICI S.P.A., Milan (IT)

( * ) Notice: Subject to any disclaimer, the term of this patent is extended or adjusted under 35 U.S.C. 154(b) by 646 days.

(21) Appl. No.: 17/920,077

(22) PCT Filed: Apr. 21, 2021

(86) PCT No.: PCT/EP2021/060426

§ 371 (c)(1),
(2) Date: Oct. 20, 2022

(87) PCT Pub. No.: WO2021/214163

PCT Pub. Date: Oct. 28, 2021

(65) Prior Publication Data

US 2023/0165820 A1 Jun. 1, 2023

(30) Foreign Application Priority Data

Apr. 21, 2020 (EP) .................................... 20170737

(51) Int. Cl.
*A61K 31/192* (2006.01)
*A61K 31/195* (2006.01)
*A61P 25/04* (2006.01)

(52) U.S. Cl.
CPC .......... *A61K 31/192* (2013.01); *A61K 31/195* (2013.01); *A61P 25/04* (2018.01)

(58) Field of Classification Search
CPC .............................. A61K 31/192; A61P 25/04
See application file for complete search history.

(56) References Cited

FOREIGN PATENT DOCUMENTS

| | | | | |
|---|---|---|---|---|
| BE | 882889 | | 8/1980 | |
| BE | 882889 | A * | 8/1980 | ............ C07C 59/84 |
| EA | 019992 | | 7/2014 | |
| EP | 3670489 | | 6/2020 | |
| EP | 3670489 | A1 * | 6/2020 | ........... A61K 31/192 |
| EP | 3842408 | | 6/2021 | |
| GB | 1497044 | | 1/1978 | |
| GB | 1497044 | A * | 1/1978 | ............ C07C 57/30 |
| WO | WO 96/074.12 | | 3/1996 | |
| WO | WO 2010/102862 | | 9/2010 | |
| WO | WO 2011/075688 | | 6/2011 | |
| WO | WO-2011075688 | A1 * | 6/2011 | ............ A61K 31/00 |
| WO | WO-2016075704 | A2 * | 5/2016 | |
| WO | WO2020126088 | | 6/2020 | |

OTHER PUBLICATIONS

Package leaflet: information for user, Gabapentin 100 mg capsules, hard Gabapentin 300 mg capsules, hard Gabapentin 400 mg capsules hard.*
Ong et al., Current technologies for the production of (S)-ketoprofen: Process perspective, Process Biochemistry, vol. 40, Issue 11, Nov. 2005, pp. 3526-3535.*
Loyd, Baclofen 5%, Gabapentin 5%, Ketoprofen 10%, and Lidocaine 5% in Pluronic Lecithin Organogel, IJPC, Issue: Nov./Dec. 2010—vol. 14, No. 6, available at https://ijpc.com/Abstracts/Abstract.cfm?ABS=3213.*
Hohmeier, Topical and Intranasal Analgesic Therapy in a Woman with Refractory Postherpetic Neuralgia, Case Rep Med. Apr. 9, 2015;2015:392874.*
English Tranisation of BE 882889.
International Search Report for PCT/EP2021/060426 dated Jul. 2, 2021.
Package Leaflet: Information for the User, Gabapentin 100 mg capsules, hard, Gabapentin 300 mg capsules, hard, Gabapentin 400 mg capsules, hard, Apr. 2019.
Paneral, et al., Trends in Medicine, 2012, 12, 159-167.
Tallarida, Genes & Cancer, 2011, 2(11), 1003-1008.
Deng et al. SMC Anesthesiology (2016) 16:12.
Enteshari-Moghaddam et al, Clinical Rheumatology 2019: 38, 2873-2880.
Low back pain and sciatica in over ios: assessment and management, National Institute for Health and Care Excellence NICE Guidelines 2016.
M. A. Rose, Anaesthesia, 2082, 57, pp. 451-462.
Moore et al, Cochrane Database Syst Rev. Apr. 27, 2014; (4):C0887938.
Quintero, Journal of Experimental Pharmacology 2017:9 13-21.
Ru-Rong Bil Nat. Rev. Drug Discov, Jul. 2014: 13(7): 533-548.

* cited by examiner

*Primary Examiner* — Svetlana M Ivanova
(74) *Attorney, Agent, or Firm* — HUESCHEN AND SAGE

(57) ABSTRACT

The present invention relates to a synergistic admixture of Gabapentin and Ketoprofen, preferably Ketoprofen Lysine, to a pharmaceutical composition comprising said admixtures and to the use of said admixtures or pharmaceutical compositions in the treatment of acute or chronic pain, in particular in the treatment of neuropathic or inflammatory pain.

14 Claims, 8 Drawing Sheets

SYNERGISTIC ADMIXTURES OF GABAPENTIN AND KETOPROFEN, PHARMACEUTICAL COMPOSITIONS AND THEIR MEDICAL USE

The present invention relates to a synergistic admixture of Gabapentin and Ketoprofen, preferably Ketoprofen Lysine, to a pharmaceutical composition comprising said admixture and to the use of said admixture or pharmaceutical composition in the treatment of acute or chronic pain, in particular in the treatment of neuropathic or inflammatory pain.

BACKGROUND ART

Pain is a sensory and emotional experience usually arising from actual or potential tissue damage.

Pain conditions can be divided in acute and chronic.

Acute pain is a pain that lasts for a short period of time, typically less than 3 months, and is commonly associated with tissue injury, inflammation, a surgical procedure, childbirth, or a brief disease process.

Chronic pain has been recognized as a pain that persists past normal healing time and hence lacks the acute warning function of physiological nociception. Usually pain is classified as chronic when it lasts or recurs for more than 3 months.

Chronic pain may have different etiologies and includes neuropathic pain, chronic inflammatory pain, for example arthritis, or pain of unknown origin, as fibromyalgia and restless leg syndrome.

Chronic neuropathic pain is caused by a lesion or disease of the somatosensory nervous system that provides information about the body including skin, musculoskeletal, and visceral organs. A number of diseases or pathological conditions can cause a damage to the sensory neurons resulting in hyperalgesia or allodynia, such for example in lower back pain, sciatalgia, post-operative pain, cancer pain, phantom limb pain, HIV pain, diabetic neuropathy pain, Herpes Zoster pain or trigeminal neuralgia.

Chronic inflammatory pain is associated to strong inflammation of infectious, autoimmune or metabolic etiology, such as rheumatoid arthritis, and by structural changes affecting bones, joints, tendons, or muscles, such as osteoarthrosis. Therapy of this type of pain usually includes the use of non-steroidal anti-inflammatory drugs, acetaminophen, and other disease-modifying agents.

Because of its complex etiology, the pharmacological treatment of neuropathic pain differs from the treatment of non-neuropathic pain. Guidelines recommend the use of serotonin and norepinephrine reuptake inhibitors, tricyclic antidepressants, anticonvulsants, or topical lidocaine treatment as first-line and second-line medications for the management of neuropathic pain, with opioids usually recommended as second- or third-line therapies (Deng et al. BMC Anesthesiology (2016) 16:12). Acetaminophen and non-steroidal anti-inflammatory drugs are largely ineffective in neuropathic pain.

Neuroinflammation is a physiological/pathological condition characterized by infiltration of immune cells, activation of glial cells and production of inflammatory mediators in the peripheral and central nervous system.

Recent progress indicates that the development of neuroinflammation of tissue is within the peripheral nervous system (PNS) and central nervous system (CNS)—is responsible for generating and sustaining the sensitization of nociceptive neurons leading to chronic pain. Neuroinflammation occurs in the PNS (that is, peripheral nerves and ganglia) and CNS (that is, spinal cord and brain) and is characterized by infiltration of leukocytes and increased production of inflammatory mediators at these sites. The trafficking of different types of leukocytes in the PNS and CNS occurs with different temporal profiles. Neuroinflammation manifests as activation of glial cells, such as Schwann cells in the nerve, satellite glial cells in the ganglia and microglia, and astrocytes and oligodendrocytes in the spinal cord and brain. Activation of glial cells leads to the production of glial mediators that can modulate pain sensitivity.

Neuroinflammation is a local inflammation which means that it is more effective at eliciting and sustaining pain than systemic inflammation, yet it is difficult to detect in clinic. For example, fibromyalgia, a chronic muscle pain condition, was previously regarded as an atypical pain, because no obvious pathologies and inflammation could be detected in affected patients. However, a recent study identified neuropathy of small nerve fibres in patients with fibromyalgia, which could be a result and also a cause of chronic neuroinflammation. Neuroinflammation appears to be permanent in patients with chronic pain but also occurs in non-chronic conditions such as for example post-surgical pain.

The lack of efficacy of currently available therapies in the management of neuroinflammatory conditions call for the identification of novel specific and safe drugs for the treatment of still unmet medical needs associated with acute or chronic neuro-inflammatory processes (Ru-Rong Jil Nat. Rev. Drug Discov. 2014 July; 13(7): 533-548).

Gabapentin is an anticonvulsant synthetic analogue of the neurotransmitter gamma-aminobutyric acid (GABA) having the following formula (I)

(I)

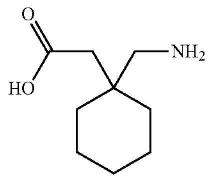

Although its exact mechanism of action is unknown, Gabapentin appears to inhibit excitatory neuron activity. The molecule was originally developed as a chemical analogue of gamma-aminobutyric acid to reduce the spinal reflex for the treatment is of spasticity but it was found to have no activity on the GABAergic system. Its mechanism of action includes binding to calcium channels in several areas of the central nervous system and spinal cord in which these channels are expressed. Calcium channels are localized on presynaptic terminals, where they control neurotransmitter release.

Gabapentin was approved for use as an adjunct treatment for partial epileptic seizures in adults and children in 1993. More recently, Gabapentin has also been approved for the treatment of chronic pain, in particular neuropathic pain syndromes. It was also claimed to be beneficial in several other clinical disorders such as anxiety, bipolar disorder, and hot flashes. Gabapentin was also proven effective at high dosage in the treatment of fibromyalgia (Moore et al, Cochrane Database Syst Rev. 2014 Apr. 27; (4):CD007938; Deng et al., BMC Anesthesiology (2016) 16:12).

However, a number of studies have demonstrated an unsatisfactory pharmacological and pharmacokinetic profile when Gabapentin is used alone in pain therapy, for instance in terms of scarce efficacy on specific types of pain, side effects or delayed onset of the response. In fact, Gabapentin is absorbed slowly after oral administration, and it has an utmost level in plasma within 3-4 hours (Quintero, Journal of Experimental Pharmacology 2017:9 13-21).

The plasma level of gabapentin does not increase proportionally if its dosages are increased, thus requiring careful titration on individual basis at the start of a treatment; gabapentin does not attach to plasma proteins.

Gabapentin is neither inhibited nor metabolized by hepatic enzymes; besides, gabapentin can be expelled by the renal system, and its excretion half-life is roughly 6 hours. The most common side effects of gabapentin are somnolence (20%), dizziness (18%), ataxia (13%) and fatigue (11%).

Oral doses of gabapentin are administered three times a day (tds) because of its short half-life. Rapid titration may be achieved with doses of 300 mg once daily (often at bedtime to minimise sedation) on the first day followed by 300 mg twice daily on the second day and 300 mg tds on the third day. Dosage may be further increased if efficacy is not achieved at this dose.

The recommended starting dose in the treatment of neuropathic pain is 300 mg three times a day with titration if necessary to a maximum of 3600 mg.day-1 but doses up to 4200 mg, have been reported when limited or no efficacy is observed (M. A. Rose, Anaesthesia, 2002, 57, pages 451-462).

For example, Gabapentin is not recommended for the treatment of lower back pain because it demonstrates little efficacy together with increased risk of side effects (Low back pain and sciatica in over 16s: assessment and management, National Institute for Health and Care Excellence NICE Guidelines 2016).

Furthermore, Gabapentin is little active on inflammatory pain, as also confirmed in the present experimental part in the Carrageenan inflammatory rat model.

It was also shown that the therapeutic effect of Gabapentin in the treatment of osteoarthritis starts only after a prolonged administration of 3 months (Enteshari-Moghaddam et al, Clinical Rheumatology 2019: 38, 2873-2880).

The Applicant has undertaken studies, with the aim of improving the activity of Gabapentin on pain conditions, extending the efficacy to other pain syndromes and possibly reducing dose related side effects.

In particular, the Applicant has carried out investigations on Gabapentin combined with Ketoprofen, specifically with Ketoprofen Lysine.

Ketoprofen ((RS)-2-(3-benzoylphenyl)-propionic acid), is a well-established nonsteroidal anti-inflammatory drug (NSAID) with analgesic and antipyretic effects having formula II (II)

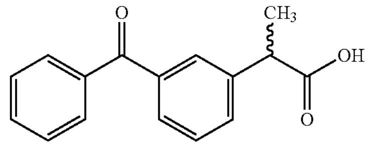

Because of its high tolerability, Ketoprofen is one of the non-steroidal anti-inflammatory drugs of widespread use in clinics, both for the treatment of serious inflammatory conditions and for its use in analgesic and antipyretic by inhibiting the body's production of prostaglandin, prostacyclines and thromboxane.

Ketoprofen is generally prescribed for arthritis-related inflammatory pains, severe toothaches, treatment of musculoskeletal pain, neuropathic pain such as sciatica, post herpetic neuralgia and referred pain for radiculopathy.

Ketoprofen pharmaceutical compositions of current use contains the racemate as active ingredient, where the two enantiomers S(+) and R(−) are present in equimolecular ratio.

Current Ketoprofen pharmaceutical compositions for oral use contain the active ingredient as free acid, which shows very low solubility in water, and therefore a low bioavailability.

In order to improve dissolution and bioavailability of the active ingredient, salts of Ketoprofen are also advantageously employed. These salts are used for example in the treatment by oral administration of those pathological symptoms of rheumatoid and chronic type, which require the drug to be administered at high dosage, continuously and for long period of time and in pain manifestation that require an immediate analgesic effect.

In particular, the salt of Ketoprofen with Lysine, in particular with the natural aminoacid L-Lysine, although presenting a parallel pharmaceutical profile and a similar anti-inflammatory-analgesic potency compared to the free acid, offers the advantage of a considerably higher solubility in water that enables rapid and almost complete absorption of the compound ensuring a rapid onset of action, and a greater gastric tolerability.

Depending on process conditions, Ketoprofen and Lysine can combine forming either a salt or co-crystals, in different crystalline forms (polymorphs), as described in the European Patent Applications n. EP18215336.1 PCT/EP20191025464 and EP19219293.8.

SUMMARY OF THE INVENTION

The Applicant during these investigations has unexpectedly found that admixtures of Gabapentin and Ketoprofen, preferably in the form of Ketoprofen Lysine salt or co-crystals, show surprising biological effects.

In this respect, the Applicant has observed a synergistic effect on inflammation and pain when Gabapentin is combined with Ketoprofen.

In addition, the combination of Gabapentin with Ketoprofen prolongs the duration of the effects on inflammation and pain.

Finally, the administration of Gabapentin in combination with Ketoprofen increases Gabapentin brain penetration in comparison with Gabapentin alone.

The higher efficacy, increased brain penetration and duration of the present combination are predictive of lower therapeutic doses of Gabapentin, of a reduced frequency of administration and thus of less side effects, with an overall improvement of patient compliance.

It is thus a first object of the present invention an admixture of Gabapentin and Ketoprofen, wherein said Ketoprofen is preferably Ketoprofen Lysine.

A further object of the present invention is the admixture of the invention for use as a medicament, preferably for use in the in the prevention, reduction or treatment of pain and/or inflammation.

A further object of the present invention is a pharmaceutical composition comprising the admixture of the invention and at least a pharmaceutically acceptable excipient.

A further object of the present invention is the pharmaceutical composition of the invention further comprising at least another pharmaceutically active ingredient.

A further object of the present invention is a kit comprising Gabapentin and Ketoprofen, preferably Ketoprofen Lysine.

A further object of the present invention is a method for the treatment of pain and/or inflammation comprising administering to the patient, simultaneously, separately or sequentially, an effective amount of Gabapentin and of Ketoprofen, preferably of Ketoprofen Lysine.

Definitions

For the purpose of the present invention, the term "pharmaceutically acceptable excipient" refers to a substance devoid of any pharmacological effect of its own and which does not produce adverse reactions when administered to a mammal, preferably a human.

For the purpose of the present invention, the term "admixture" refers to a physical admixture or blend of at least two ingredients, which can be manufactured by e.g. simple dry mixing. A physical admixture does not consist of complexes or co-crystals possibly obtainable from the ingredients under conditions other than dry mixing, such as for instance by co-crystallization, wet mixing or co-grinding. The ingredients of the admixture at a molecular level are not within a single crystal.

For the purpose of the present invention, the term "Ketoprofen Lysine" refers both to the salt Ketoprofen Lysinate and to the co-crystals of Ketoprofen with Lysine, in any polymorph or solvated form, preferably to the co-crystals as described in the European Patent Application n. EP18215336.1, PCT/EP2019/025464 and EP19219293.8.

For the purpose of the present invention, the term "Ketoprofen Lysine co-crystal Form I" refers to the co-crystal described in EP18215336.1 and PCT/EP2019/025464.

For the purpose of the present invention, the term "Ketoprofen Lysine co-crystal Form IV" refers to the co-crystal described in EP19219293.8.

For the purpose of the present invention, the term "Ketoprofen Lysinate" refers to the salt of Ketoprofen with Lysine.

For the purpose of the present invention, the term "room temperature" means a temperature range of 18 to 25° C.

For the purpose of the present invention, the term "co-crystal" means a multi-component system, in which all components are solid under ambient conditions when in their pure form. The components coexist at a molecular level within a single crystal. At least some the components are connected by non-covalent, non-ionic interactions.

For the purpose of the present invention, the term "pain" means pain caused by disturbances of different nature and origin, such as, for example: headache or cephalalgia: both primary and therefore not related to other factors or diseases, and secondary and therefore dependent on trauma, injury and distinct diseases; toothache: in case of abscesses or caries that create pain in the dental pulp, with numerous blood vessels and nerves; menstrual pains: abdominal and lower abdominal pain and headaches caused by hormonal changes typical of the period of menstruation; neuralgia, or intense nerve pain due to strains, trauma and infections; pain in the muscles, or myalgia: pains located at the level of muscles when using or touching them, due to sudden contractions or traumas; osteoarticular pains, such as joint inflammations (to the bones, cartilages, ligaments and tendons) following traumas, old age, strains and injuries.

For the purpose of the present invention, the term "inflammation" means the local response of an organism to cellular injury that is marked by capillary dilatation, leukocytic infiltration, redness, heat, and pain and that serves as a mechanism initiating the elimination of noxious agents and of damaged tissue.

The terms "approximately" and "about" herein refers to the range of the experimental error, which may occur in a measurement.

Keys in the Figures: GAB Gabapentin; KL Ketoprofen Lysine; Co-xx co-crystal; MIX admixture; KL Co-xx Ketoprofen Lysine co-crystal; K-L-GAB Co-xx Ketoprofen Lysine Gabapentin co-crystal; KL Co-xx-GAB MIX admixture of Ketoprofen Lysine co-crystal with Gabapentin.

DETAILED DESCRIPTION OF THE INVENTION

An object of the present invention is an admixture of Gabapentin and Ketoprofen, preferably and admixture of Gabapentin with Ketoprofen Lysine.

Preferably, the molar ratio of the components of the admixture is comprised between 100:1 and 1:100, between 50:1 and 1:50, more preferably between 20:1 and 1:20, even more preferably between 10:1 and 1:10, still more preferably between 5:1 and 1:5, most preferably between 2:1 and 1:2. In one preferred embodiment, the molar ratio in the admixture is about 1.1.

Figure 1:
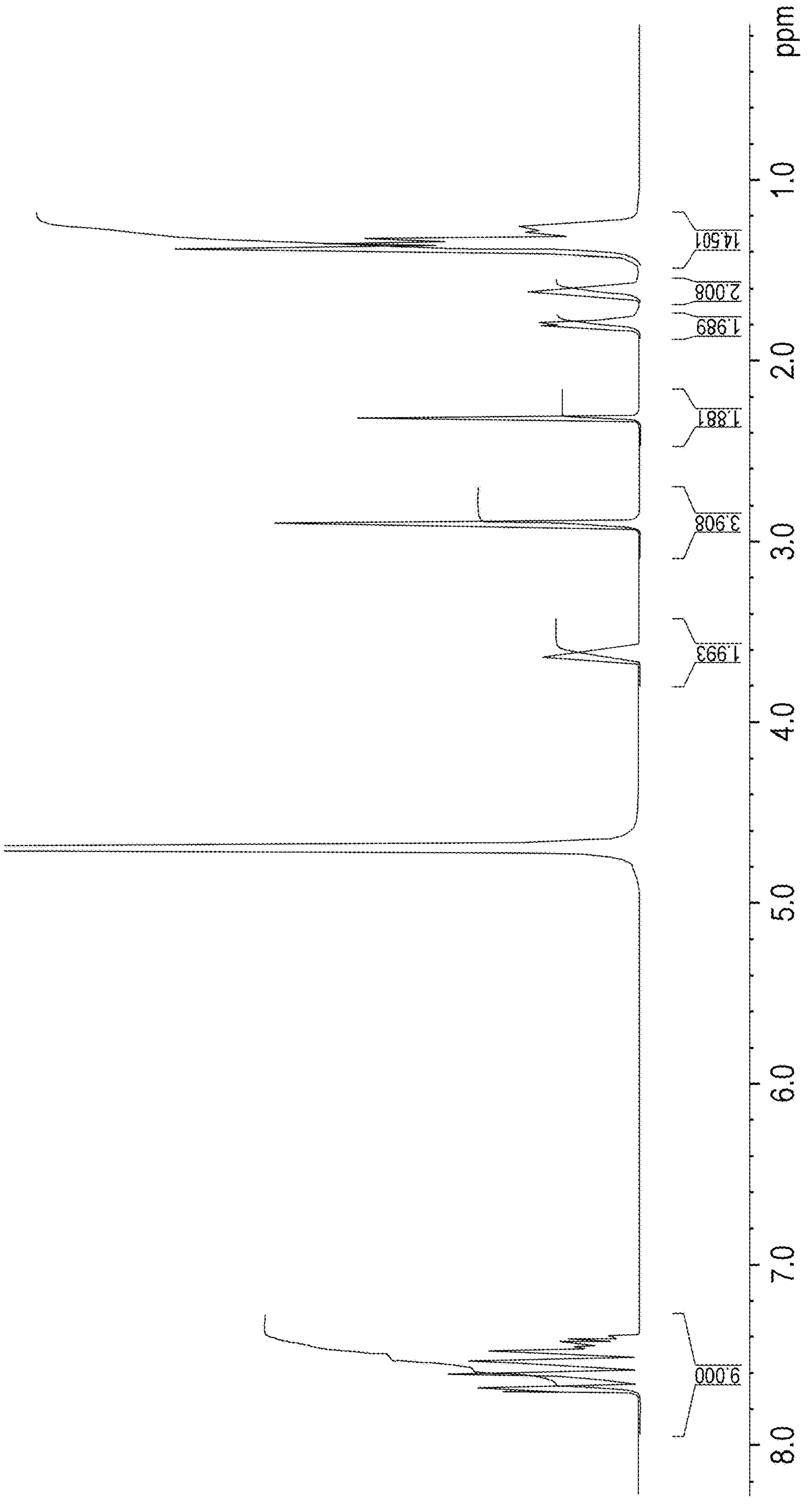
FIG. 1: $^1$H-NMR spectrum (400 MHz, D20) of a 1:1 admixture of Ketoprofen Lysine co-crystal Form I and Gabapentin.

A 1:1 admixture of the present invention is characterized by the 1H-NMR of FIG. 1 and relative assignments in Table 2.

In the present admixture, Gabapentin can be in any crystalline form.

In the present admixture, Gabapentin can be used either in its neutral form (zwitterionic internal salt) or in any acid or basic salified form, for instance as Gabapentin hydrochloride or Gabapentin Sodium salt.

Preferably, Gabapentin is used in its neutral form.

Gabapentin can be in any polymorph form.

In the present admixture, Ketoprofen can be used as free acid, as a salt with pharmaceutically acceptable bases or as a co-crystal.

Examples of Ketoprofen salts are Ketoprofen Sodium, Ketoprofen Trometamol or a Ketoprofen salt with a basic aminoacid such as Lysine.

In the admixture of the invention, Ketoprofen can be racemic (S,R) Ketoprofen, (S)-Ketoprofen or (R)-Ketoprofen or any admixture thereof.

In one embodiment, Ketoprofen is (S)-Ketoprofen (also named DexKetoprofen).

Preferably, in the admixture of the invention, Ketoprofen is Ketoprofen Lysine.

In the present admixture, Ketoprofen Lysine can be the salt Ketoprofen Lysinate, a Ketoprofen Lysine co-crystal, in any crystalline form, or a mixture thereof.

In one embodiment, Ketoprofen Lysine is a Ketoprofen Lysine co-crystal, preferably the Ketoprofen Lysine co-crystal Form I or Ketoprofen Lysine co-crystal Form IV. In one embodiment, Ketoprofen Lysine is the salt Ketoprofen Lysinate.

Ketoprofen Lysinate can be prepared as described for instance in GB1497044A and BE882889.

Ketoprofen Lysine co-crystal Form I can be prepared as described for instance in the European Patent Application n. EP18215336.1 and PCT/EP2019/025464. Ketoprofen Lysine co-crystal Form IV can be prepared as described for instance in the European Patent Application EP19219293.8.

The components of the admixture of the present invention can be in unsolvated forms as well as solvated forms, including hydrated forms. Preferably, they are in unsolvated forms.

In the Ketoprofen Lysine of the admixture of the invention Lysine can be racemic (S,R)-Lysine, (S)-Lysine or (R)-Lysine, or any admixture thereof, preferably is the natural aminoacid (S)-Lysine also named L-Lysine.

In one embodiment, said Ketoprofen is in (S) configuration.

In another embodiment, said Ketoprofen is in racemic configuration. In one embodiment, said Lysine is in (S) configuration.

In one embodiment, the admixture of the invention comprises (S)-Ketoprofen and/or (S)-Lysine.

As will be described in the Experimental section that follows, the admixture of the present invention shows an improved efficacy in pain conditions when compared to Gabapentin or Ketoprofen alone. The two active ingredients interact synergically and lead to a higher and more prolonged analgesic effect than when used individually.

In accordance with the above, the daily dosage of each active ingredient in the mixture according to the invention can be lower than that usually employed for the active ingredient when not in combination.

Accordingly, a further object of the present invention is the admixture of the invention for use as a medicament.

The medical use of the present admixture can be curative, prophylactic or palliative. Preferably, the admixture according to the invention is for use in the prevention, reduction or treatment of pain and/or inflammation.

The admixture of the present invention is preferably used for the treatment of pain, preferably of acute or chronic pain. Preferably, said pain is selected from headache, toothache, menstrual pain, muscle pain, neuropathic pain, diabetic neuropathy, cancer pain, osteoarthritis, low back pain, sciatalgia, fibromyalgia, trigeminal neuralgia; post-surgical and post-operative pain, post herpetic neuralgia, rheumatoid arthritis, ankylosing spondylitis, frozen shoulder, phantom limb pain or HIV pain.

Preferably, the admixture of the present invention is administered orally.

The association of the two active ingredients in the present admixture exhibits several advantages for the present medical use.

As discussed above, Gabapentin and Ketoprofen are complementing each other in the treatment especially of pain, but possibly also of various other diseases or symptoms.

Another advantage is that the association of two active ingredients in the admixture allows for a better Pharmacokinetic I Pharmacodynamic (PKPD) including also a better penetration of the blood-brain barrier, which greatly helps in the treatment of pain.

The admixture of the present invention shows a synergistic activity of the active ingredients Gabapentin and Ketoprofen, as demonstrated in the present pain and inflammation predictive test.

This unexpected synergy can provide enhanced clinical efficacy compared to the individual components of the admixture administered alone or a reduction in the required dose of each compound, leading to less side effects whilst maintaining or enhancing the clinical effectiveness of the compounds and treatment.

For example, the patient may experience an improved reduction in the frequency and severity of pain and/or inflammation. Furthermore, the patient may benefit from a longer duration of action from the admixture treatment than from treatment with Gabapentin or with Ketoprofen or Ketoprofen Lysine alone.

Preferably, the daily dosage of admixture according to the invention for humans is Ketoprofen, calculated as acid form, in an amount between 25 and 200 mg, preferably between 50 and 150 mg, more preferably of 50 mg and Gabapentin in an amount between 5 and 500 mg, preferably between 100 and 300 mg, more preferably of 300 mg, from 1 to 8 times per day, preferably from 1 to 4 times a day.

It is necessary for the skilled artisan, such as a physician or a veterinarian, not only to determine the preferred route of administration and the corresponding dosage form and amount, but said artisan must also determine the dosing regimen.

The daily dosage for humans and animals may vary depending on factors that have their basis in the respective species or other factors, such as age, sex, weight or degree of illness and so forth.

A further object of the present invention is a pharmaceutical composition comprising the admixture of Gabapentin and Ketoprofen as defined above and a least one pharmaceutically acceptable excipient.

Preferably said pharmaceutical composition is for use in the treatment of pain, preferably of acute or chronic pain and inflammation, preferably neuroinflammation.

Preferably, said pain is selected from headache, toothache, menstrual pain, muscle pain, neuropathic pain, diabetic neuropathy, pain associated to neuroinflammation, cancer pain, osteoarthritis, low back pain, sciatalgia, fibromyalgia, trigeminal neuralgia; post-surgical and post-operative pain, post herpetic neuralgia, rheumatoid arthritis, ankylosing spondylitis, frozen shoulder, phantom limb pain or HIV pain.

For instance, the composition according to the present invention may contain 0.5-60% by weight of the admixture as defined herein and 40-99.5% by weight of one or more pharmaceutically acceptable excipients.

The choice of the excipients will to a large extent depend on factors such as the particular mode of administration, the effect on solubility and stability, and the nature of the dosage form.

Pharmaceutical compositions according to the present invention may be in any form suitable for the administration to humans and/or animals, preferably humans including infants, children and adults and can be produced by standard procedures known to those skilled in the art. Preferably, the pharmaceutical composition according to the present invention is administered orally.

The pharmaceutical composition of the present invention preferably is for oral administration, preferably it is an oral solid or liquid composition.

Preferably said solid composition is a capsule, pellet, tablet, cachet, chewable dosage form, lozenge, granules, suspension, emulsion, spray, powder.

Said powder is preferably suitable to be reconstituted with a liquid medium.

When the pharmaceutical composition is a powder it can be prepared for instance by dry mixing the powders of each of active ingredient in conventional blenders, either fixed shell blenders (e.g., impeller mixers, ribbon or screw mixers), or rotating shell blenders (e.g., drum, cross-flow, double cone, and twin-shell) under conditions and times within the reach of the skilled person.

Preferably, said oral solid composition of the invention comprises an amount per dosage form of Ketoprofen, calculated as acid form, between 25 and 200 mg, preferably between 50 and 150 mg, more preferably of 50 mg and/or an amount per dosage form of Gabapentin between 50 and 500 mg, preferably between 100 and 300 mg, more preferably of 300 mg.

The pharmaceutical composition can additionally contain one or more pharmaceutically acceptable excipients, such as fillers, binders, glidants, disintegrants, flow regulating agents and release agents.

Suitable excipients are for example disclosed in "Handbook of Pharmaceutical Excipients", 3rd Edition, published by A. H. Kibbe, American Pharmaceutical Association, Washington, USA, and Pharmaceutical Press, London.

Suitable fillers are for example lactose (monohydrate, spray-dried monohydrate, anhydrous and the like), mannitol, xylitol, dextrose, sucrose, sorbitol, microcrystalline cellulose, starch, dibasic calcium phosphate dihydrate and calcium hydrogen phosphate.

Fillers can be present in an amount of 0-80% by weight, preferably in an amount of 10-60% by weight of the total weight of the composition.

Suitable binders are for example polyvinylpyrrolidone, microcrystalline cellulose hydroxypropyl cellulose, hydroxypropyl methylcellulose, methylcellulose, hydroxyethyl cellulose, sugars, dextran, cornstarch, gelatin, polyethylene glycol, natural and synthetic gums, pregelatinised starch.

Binders can be present in an amount of 0-80% by weight, preferably in an amount of 10-60% by weight of the total weight of the composition.

Binders are generally used to impart cohesive qualities to a tablet formulation.

Suitable glidants are for example alkaline earth metal salts of fatty acids, like stearic acid such as magnesium stearate, calcium stearate, zinc stearate, sodium stearyl fumarate, and mixtures of magnesium stearate with sodium lauryl sulphate.

The glidant can be present for example in an amount of 0-2% by weight, preferably in an amount of 0.5-1.5% by weight of the total weight of the composition.

Suitable disintegrants are for example croscarmellose sodium, sodium carboxymethyl starch, crosslinked polyvinylpyrrolidone (crosspovidone), sodium carboxymethylglycolate, sodium starch glycolate, sodium carboxymethyl cellulose, calcium carboxymethyl cellulose, polyvinylpyrrolidone, methyl cellulose, microcrystalline cellulose, lower alkyl-substituted hydroxypropyl cellulose, starch, pregelatinised starch, sodium alginate and sodium bicarbonate.

The disintegrant can be present in an amount of 0-20% by weight, preferably in an amount of 1-15% by weight of the total weight of the composition.

A suitable flow regulating agent is for example colloidal silica. The flow regulating agent can be present in an amount of 0-8% by weight, preferably in an amount of 0.1-3% by weight of the total weight of this composition.

A suitable release agent is for example talcum. The release agent can be present in an amount of 0-5% by weight, preferably in an amount of 0.5-3% by weight of the total weight of the composition.

The solid composition may be coated, preferably film coated.

A suitable coating agent are for example cellulose derivatives, poly(meth)acrylate, polyvinyl pyrrolidone, polyvinyl acetate phthalate, and/or shellac or natural rubbers such as carrageenan.

There are many situations in which it will be advantageous or even necessary to deliver the admixture of the present invention as a solid, for instance by installing a solid implant composition into suitable body tissues or cavities.

The implant may comprise a matrix of biocompatible and bioerodible materials in which particles of the admixture of the present invention are dispersed, or in which, possibly, globules or isolated cells of a liquid mixture of the present admixture are entrapped. Desirably, the matrix will be broken down and completely absorbed by the body. The composition of the matrix is also preferably selected to provide controlled-, sustained-, and/or delayed release of the admixture of the present invention over extended periods.

Alternatively, the admixture of the invention may be formulated as a solid, semi-solid, or thixotropic liquid for administration as an implanted depot providing modified release of the active compound.

The present composition can be administered topically to the skin or mucosa, that is dermally, epidermally, subepidermally or transdermally.

The present composition can be administered sublingually or via a suppository.

Typical formulations for this purpose include pour-on, spot-on, dip, spray, mousse, shampoo, powder formulation, gels, hydrogels, lotions, creams, ointments, dusting powders, dressings, foams, films, skin patches, wafers, implants, depots, sponges, fibres, bandages, microemulsions, oro-soluble granulates. Liposomes may also be used.

The pharmaceutical composition of the present invention may be a solid composition for the extemporaneous preparation of a solution for oral or parenteral administration, for example to be administered by intramuscular, intraperitoneal, or intravenous injection.

The pharmaceutical composition of the present invention can be prepared by methods well known to a person skilled in the art.

The composition of the invention may be of immediate-, delayed-, modified-, sustained-, pulsed- or controlled-release type.

According to a further embodiment, the pharmaceutical composition of the invention may comprise the admixture of the invention and at least another pharmaceutically active ingredient.

The other pharmaceutically active ingredient will be determined by the circumstances under which the therapeutic agent of the present invention is administered.

A further object of the present invention is a kit comprising Gabapentin and Ketoprofen Lysine.

Preferably, in the kit of the invention, the molar ratio of Gabapentin and Ketoprofen Lysine is comprised between 100:1 and 1:100 or 50:1 and 1:50, preferably between 20:1 and 1:20, more preferably between 10:1 and 1:10, still more preferably between 5:1 and 1:5, most preferably between 2:1 and 1:2.

In one preferred embodiment, the molar ratio in the kit is about 1:1.

A further object of the present invention is a method for the treatment of pain and/or inflammation comprising administering to the patient, simultaneously, separately or sequentially, an effective amount of Gabapentin and of Ketoprofen, preferably Ketoprofen Lysine.

Experimental Part

In the following, the manufacture of the admixture of Gabapentin and Ketoprofen of the invention, its analytical and biological characterization are described.

1. Preparation of the Admixture of Gabapentin and Ketoprofen Lysine Co-Crystal Form I The mixture was prepared by dry mixing Ketoprofen Lysine co-crystal form I, prepared as described in the European Patent Application n. EP18215336.1 and PCT/EP2019/025464 and Gabapentin (from Spectrum) in a 1:1 molar ratio in a powder mixing machine provided by Cavicchi SpA.

2. Thermal Analyses

DSC Analysis

The analysis was carried out using the instrument DSC Mettler Toledo DSC1.

The sample was weighed in an aluminum pan hermetically sealed with an aluminum cover. The analysis was performed by heating the sample from 25° C. to 320° C. at 10K/min, under the conditions shown in Table 1 below:

TABLE 1

| Temperature Data | |
|---|---|
| Temperature range | −40° C. to 450° C. |
| Temperature accuracy | ±0.2K |
| Temperature precision | ±0.02K |
| Furnace temperature resolution | ±0.00006K |
| Heating rate | 0.02 to 300K/min |
| Cooling rate | 0.02 to 50K/min |
| Cooling time | 5 min (100° C. to 0° C.) |

TABLE 1-continued

| Calorimetric Data | |
|---|---|
| Sensor type | FRS5 |
| Sensor material | Ceramic |
| Number of thermocouples | 56 |
| Signal time constant | 1.8 s |
| Indium peak (height to width) | 17 |
| TAWN resolution | 0.12 |
| Sensitivity | 11.9 |
| Resolution | 0.04 μW |
| Digital resolution | 16.8 million points |

Figure 2:
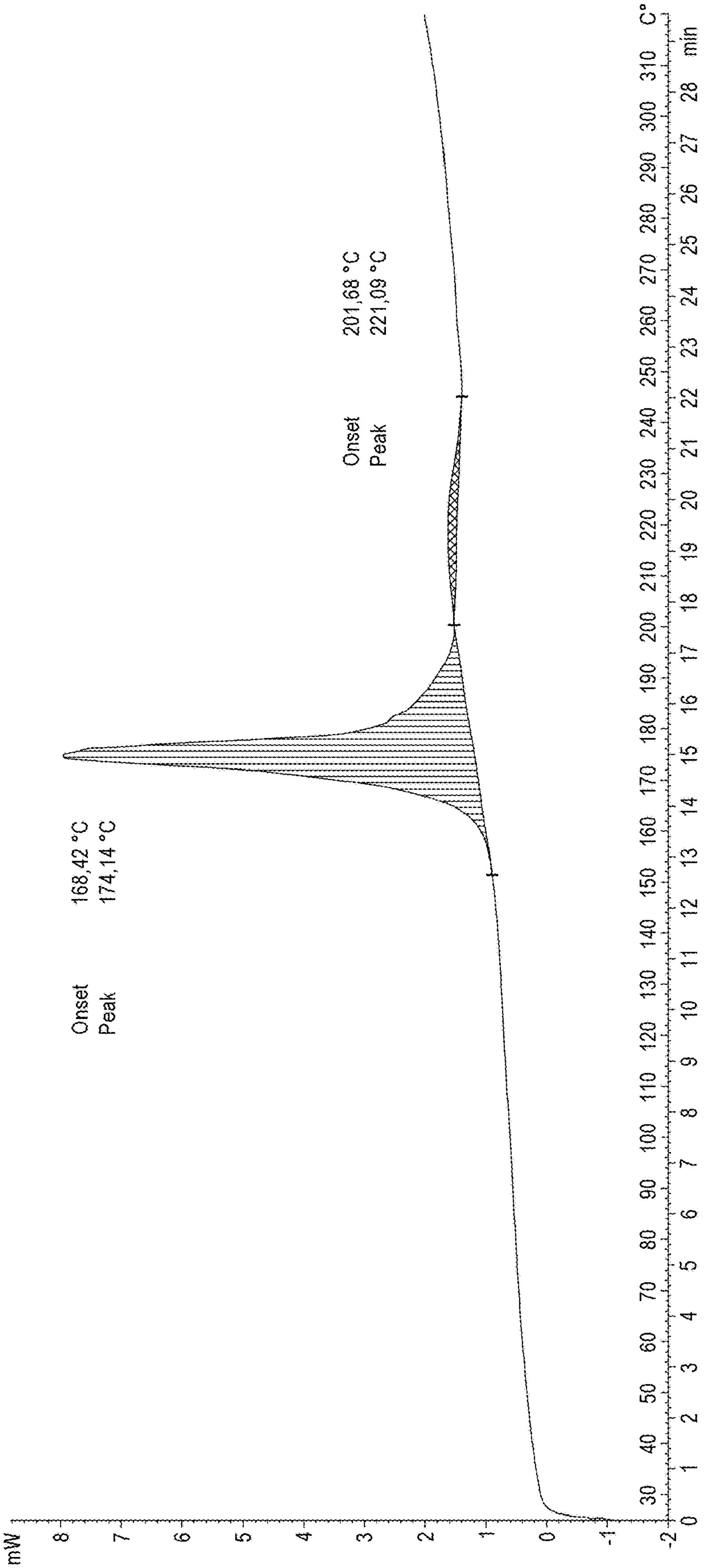
FIG. 2: DSC thermogram of Ketoprofen Lysine co-crystal Form I.
Figure 3:
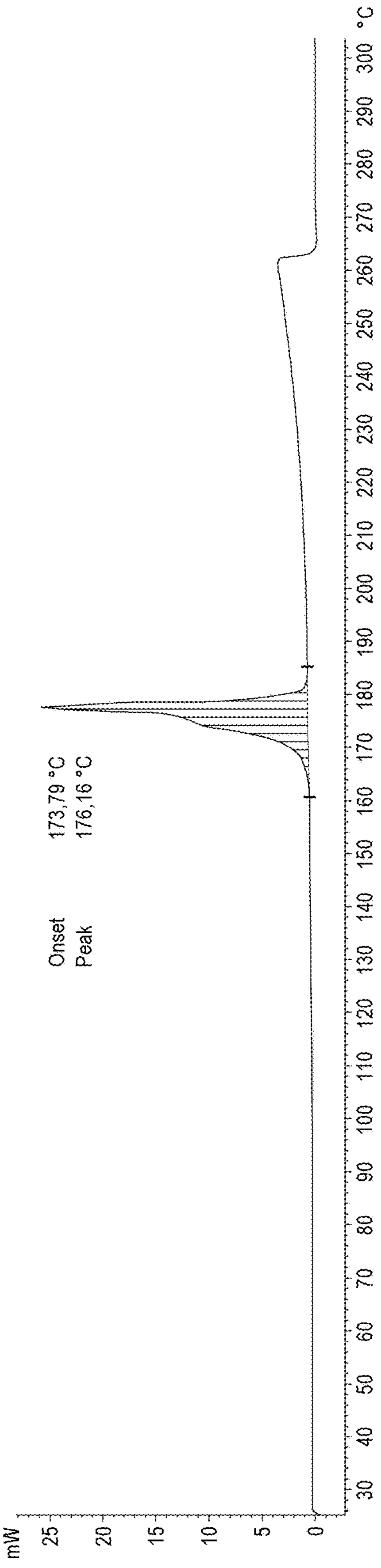
FIG. 3: DSC thermogram of Gabapentin.

The analysis was carried out on samples of Ketoprofen Lysine co-crystal form I (FIG. 2) and of Gabapentin (FIG. 3).

3. NMR Analysis $^{1}$H-Nuclear magnetic resonance (NMR) spectra were recorded in the indicated solvent with tetramethylsilane (TMS) as internal standard on a Bruker Avance3 400 MHz instrument. Chemical shifts are reported in parts per million (ppm) relative to the internal standard. Abbreviations are used as follows: s=singlet, d=doublet, t=triplet, q=quartet, m=multiplet, dd=doublets of doublet, br=broad. Coupling constants (J values) are given in hertz (Hz).

$^{1}$H-NMR Spectra of the Admixture of Ketoprofen Lysine Co-Crystal Form I and Gabapentin $^{1}$H-NMR spectrum of Ketoprofen Lysine co-crystal form I and Gabapentin admixture confirmed the concomitant presence in the sample of Ketoprofen Lysine co-crystal form I and Gabapentin with 1:1 molar ratio.

The multiplicity and the assignment of the signals are reported in Table 2 below:

TABLE 2

| $^{1}$H-NMR | | |
|---|---|---|
| δ ppm | Multiplicity | Assignment |
| 7.76-7.78 | m, 2H | Ar KET |
| 7.68-7.72 | m, 2H | Ar KET |
| 7.60-7.63 | m, 2H | Ar KET |
| 7.47-7.57 | m, 3H | Ar KET |
| 3.70 | t, J = 6.4 Hz, 1H | CH-LYS |
| 3.69 | quart, J = 7.2 Hz, 1H | CH-KET |
| 2.98 | t, J = 7.6 Hz, 2H | $CH_2$-LYS |
| 2.96 | s, 2H | $CH_2$-GAB |
| 2.38 | S, 2H | $CH_2$-GAB |
| 1.79-1.92 | m, 2H | $CH_2$-LYS |
| 1.68 | quint., J = 7.6 Hz, 2H | $CH_2$-LYS |
| 1.40 | d, J = 7.2 Hz, 3H | $CH_3$-KET |
| 1.29-1.52 | m, 12H | 5 $CH_2$-GAB; $CH_2$-LYS |

The $^{1}$H-NMR spectrum (400 MHz, D20) of Ketoprofen Lysine co-crystal form I and Gabapentin admixture is shown in FIG. 1.

4. In Vivo Studies

Inflammatory Pain in Rats Induced by Carrageenan Intraplantar Injection

Male Wistar rats (270-280 g) (Envigo, Italy), were housed 2-3 per cage under controlled illumination (12:12 h light: dark cycle; light on 06.00 h) and standard environmental conditions (room temperature 22±1° C., humidity 60±10%) for at least 1 week before experimental use. Rat chow and tap water were available ad libitum. The experimental procedures were approved by the Animal Ethics Committee of University of Campania "Luigi Vanvitelli". Animal care was in compliance with Italian Legislative Decree (D.L. 116/92) and European Commission Directive (O.J. of E.C. L358/1, 18/12/86) regulations on the protection of laboratory animals. All efforts were made to minimize animal suffering and the number of animals used.

Peripheral inflammatory pain was induced in the left hind paw of each animal by a single intraplantar injection of 1% λ-carrageenan (100 μl for each rat in 0.9% NaCl). Vehicle (2 capsules filled with Avicel PH101), Ketoprofen Lysine co-crystal form I (47.1 mg/kg, 1 capsule), Gabapentin (20.4 mg/kg, 2 capsules) and the 1:1 admixture of Gabapentin and Ketoprofen Lysine co-crystal form I (47.1 mg/Kg+20.4 mg/Kg, 2 capsules) were orally administered 1 h before the carrageenan injection. The paw volume of the animals was measured by Plethysmometer (Ugo Basile, Varese, Italy) before (0 h) and after injection of carrageenan at different time intervals (1, 2, 3, 4, 5 and 6 h post-carrageenan). Edema was expressed as the mean increase in paw volume (ml) relative to control animals. The percentage inhibition of edema was calculated by the following equation:

$$\%\ \text{inhibition of edema} = (Vc - Vt/Vc) \times 100,$$

where Vc is the edema volume in the control group and Vt is the edema volume in treated group.

Figure 4:
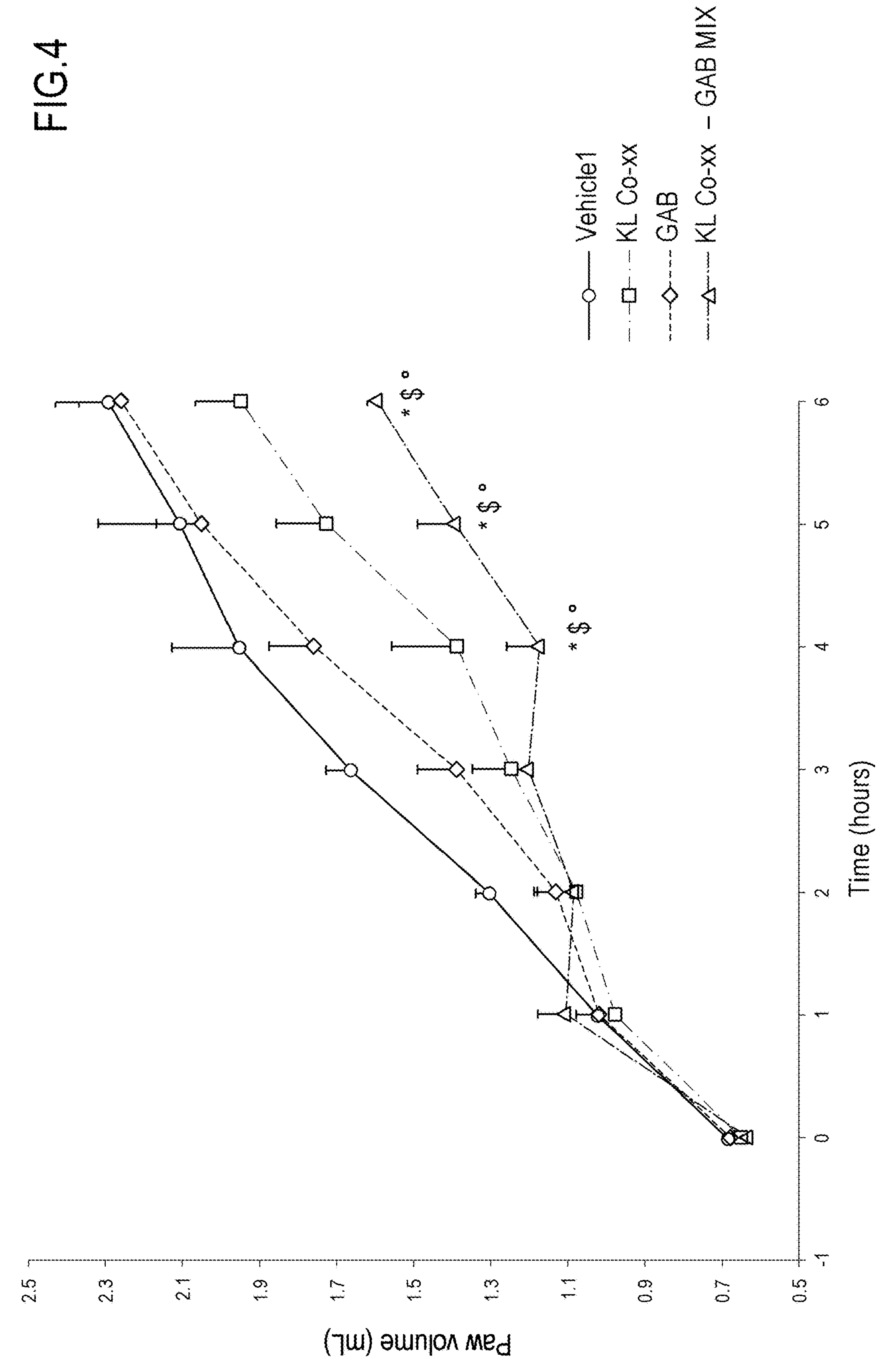
FIG. 4: graph of paw volume (ml) versus time (hours) in carrageenan-induced rat paw edema model after intraplantar injection of 1% of carrageenan followed by administration of Vehicle, a 1:1 admixture of Ketoprofen Lysine co-crystal Form I and Gabapentin (KL Co-xx-GAB MIX), Ketoprofen Lysine co-crystal Form I (KL Co-xx) or Gabapentin (GAB). P<0.05 was considered as statistical significance and calculated by using two-way ANOVA followed by Bonferroni post-hoc test. *vs Vehicle, $ vs Gabapentin, ° vs KL Co-xx
Figure 5:
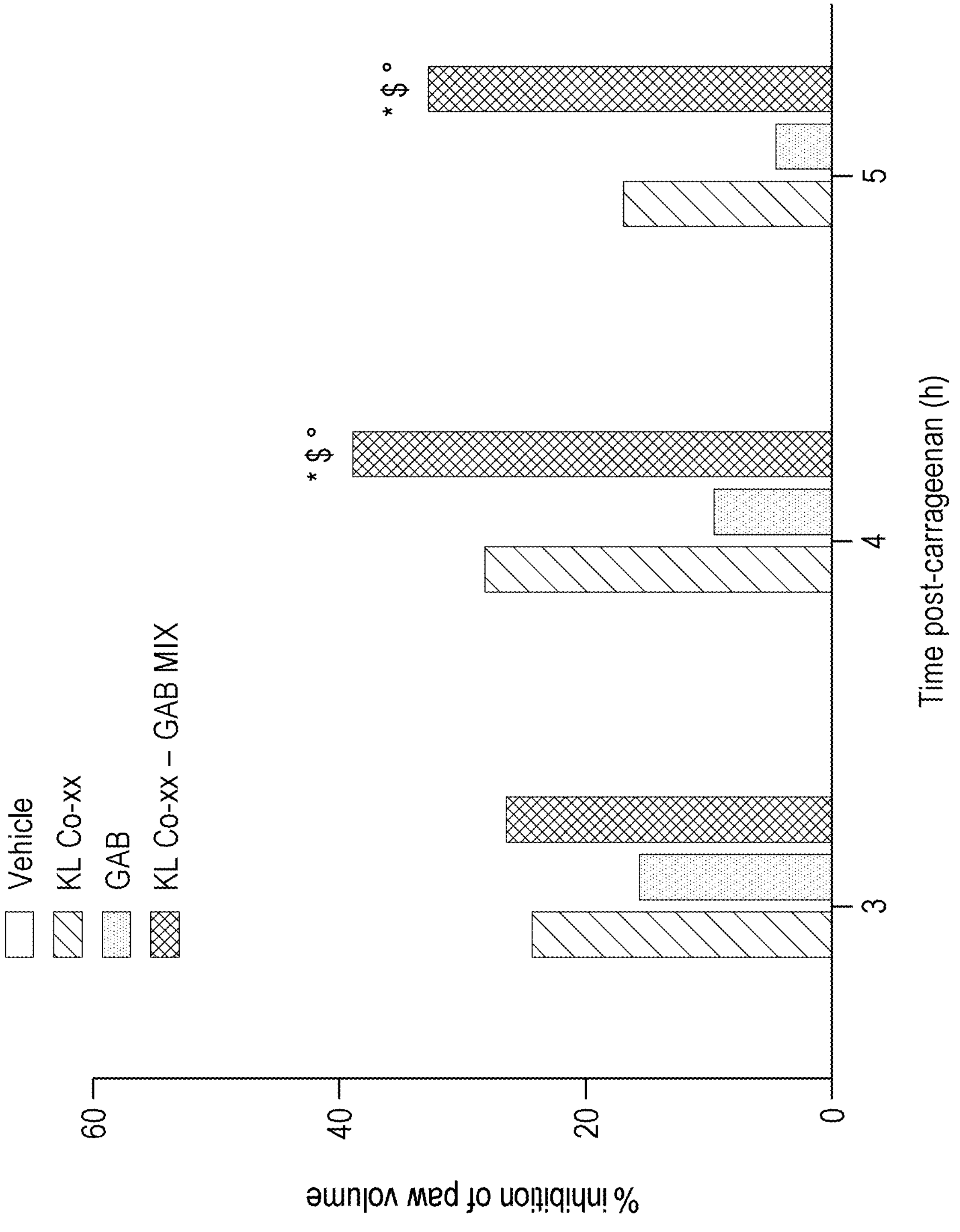
FIG. 5: bar chart of % inhibition of paw volume in carrageenan-induced rat paw edema model induced by Vehicle, a 1:1 admixture of Ketoprofen Lysine co-crystal Form I and Gabapentin (KL Co-xx-GAB MIX), Ketoprofen Lysine co-crystal Form I (KL Co-xx), Gabapentin (GAB) at 3, 4 and 5 hours post-carrageenan injection. In the chart, the value of the % of inhibition for the vehicle is zero. P<0.05 was considered as statistical significance and calculated by using two-way ANOVA followed by Bonferroni post-hoc test. *vs Vehicle, $ vs Gabapentin, ° vs KL Co-xx

The results of the above tests are shown in the graphs of FIGS. 4 and 5.

In FIG. 4 the graph of the time-course of the anti-inflammatory effect of the 1:1 admixture of Gabapentin and Ketoprofen Lysine co-crystal form I compared with Ketoprofen Lysine co-crystal Form I, Gabapentin and Vehicle on rat paw swelling (paw volume in ml) after intra-plantar injection of 1% of carrageenan is reported.

In FIG. 5 the bar graph of the % inhibition of the paw volume induced by the 1:1 admixture of Gabapentin and Ketoprofen Lysine co-crystal form I compared with Ketoprofen Lysine co-crystal form I, Gabapentin and Vehicle, at 3, 4 and 5 hours post-carrageenan injection is reported.

In the graphs of FIGS. 4 and 5, each time point or bar represents the mean±SEM of six rats per vehicle and eight rats per drug. $P<0.05$ was considered as statistical significance and calculated by using two-way ANOVA followed by Bonferroni post-hoc test. Keys: *vs Vehicle, $ vs Gabapentin, 0 vs Ketoprofen Lysine co-crystal.

From the graphs of FIGS. 4 and 5, it appears that Ketoprofen Lysine co-crystal Form I attenuated carrageenan-evoked edema while Gabapentin was less effective.

Furthermore, it resulted that the anti-inflammatory effect of the 1:1 admixture of Ketoprofen Lysine co-crystal Form I and Gabapentin of the invention was not only higher than the sum of the effects of the single actives Gabapentin and Ketoprofen Lysine co-crystal form I but, even more unexpectedly, it lasted much longer, as it can be appreciated from the rat paw edema curves of FIG. 4 and from the % inhibition bars of FIG. 5. This trend is predictive of an efficacy over an extended time, longer than that of the individual actives given alone.

Neuropathic Pain Induced by Nerve Ligation

The testing substances were provided by Dompe Farmaceutici S.p.A., Gabapentin was purchased from Spectrum (Cat#G1092), and the rice starch used in the vehicle control group was obtained from Sigma (Cat#S7260).

Gabapentin alone, Ketoprofen Lysine co-crystal form I alone or the 1:1 admixture of Gabapentin and Ketoprofen Lysine co-crystal form I of the invention were administrated orally via Torpac® Size 9 gelatin capsule(s). For each rat, 1-3 capsule(s) were given based on the proposed dosages.

Male Sprague Dawley rats weighing 180±20 g were provided by BioLasco Taiwan (under Charles River Laboratories Licensee). Space allocation for 2-3 animals was 45×25×21 cm. All animals were maintained in a controlled temperature (20-24° C.) and humidity (30%-70%) environment with 12 hr light/dark cycles. Free access to standard lab diet [MFG (Oriental Yeast Co., Ltd., Japan)] and autoclaved water were granted. All aspects of this work including housing, experimentation, and animal disposal were performed in general accordance with the "Guide for the Care and Use of Laboratory Animals: Eighth Edition" (National Academies Press, Washington, D.C., 2011) in our AAALAC-accredited laboratory animal facility. In addition, the animal care and use protocol was reviewed and approved by the IACUC at Pharmacology Discovery Services Taiwan, Ltd.

On Day 0, under pentobarbital sodium [50 mg/kg, intraperitoneally (IP)] anesthesia, the left sciatic nerve was exposed at mid-thigh level. Four chromic gut ligatures, about 1 millimeter (mm) apart, were loosely tied around the nerve. The animals were then housed socially in cages with soft bedding for 13 days before the assessment for mechanical allodynia.

The rats were placed under inverted Plexiglas cages on a wire mesh rack and allowed to acclimate for 20 to 30 minutes. Mechanical allodynia threshold was assessed by the manual von Frey test using the Chaplan up/down method. The animals were given 20-30 minutes to acclimatize to the wire mesh rack in individual compartments prior to the behavioral testing. The paw was touched with a series of 8 manual von Frey monofilaments with logarithmically incremental stiffness [3.61 (0.4 g), 3.84 (0.6 g), 4.08 (1.0 g), 4.31 (2.0 g), 4.56 (4.0 g), 4.74 (6.0 g), 4.93 (8.0 g), and 5.18 (15.0 g)]. The manual von Frey monofilament was applied perpendicularly from underneath the mesh floor to the central plantar surface with sufficient force to cause a slight buckling against the paw, and held for approximately 6-8 seconds. A positive response was noted if the paw was sharply withdrawn; ambulation was considered an ambiguous response, and in such cases, the stimulus was reapplied. Mechanical threshold [50% withdrawal threshold (g)] was assessed using the up/down method following the procedure described by Chaplan (1994).

The resulting pattern of positive and negative responses was tabulated using the convention, X=withdrawal; O=no withdrawal and the 50% response threshold was interpolated using the formula:

$$\text{Mechanical threshold} = (10[Xf + k\delta])/10{,}000,$$

where Xf=value (in log units) of the final von Frey hair used;

k=tabular value for the pattern of positive/negative responses; and

δ=mean difference (in log units) between stimuli (here, 0.224).

All rats were assessed for mechanical allodynia for pre-surgical allodynia thresholds on Day −1 (pre-surgery baseline). The rats were pre-selected for experimentation only if the pain threshold on Day 13 after nerve ligation (pre-treatment) was reduced by 10 g of force relative to the response of the individual paw before nerve ligation (pre-surgery), namely, with clear presence of allodynia. The rats were randomized based on pre-dose mechanical allodynia scores to balanced treatment groups. The compounds were administered orally (PO) by the size 9 gelatin capsule(s) or in the proposed formulation. The mechanical allodynia was assessed again at 1, 3 and 6 hour(s) following administration of the test article, vehicle or reference compound on Day 14 post-surgery.

Figure 6A:
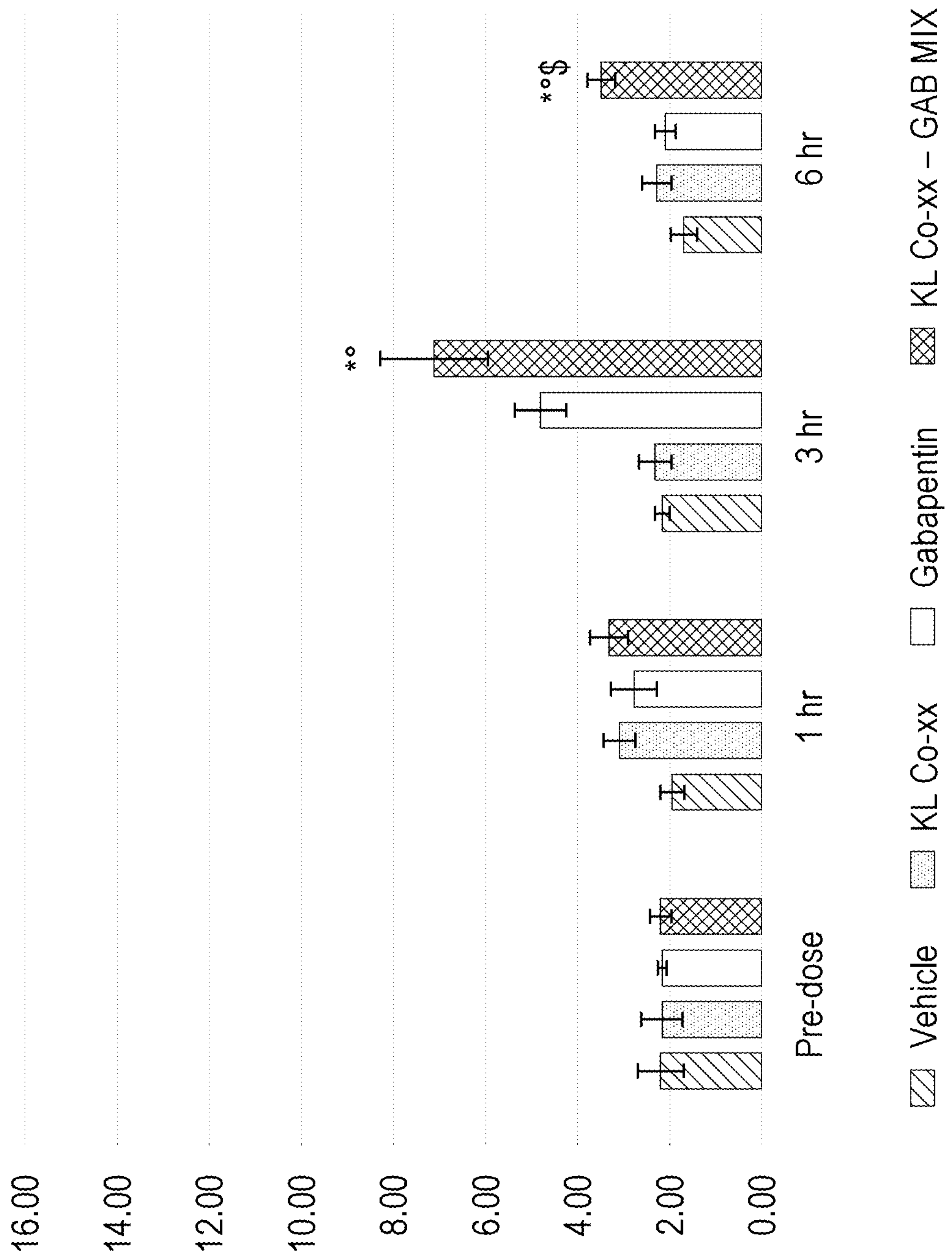
FIG. 6: bar chart illustrating the effect of treatment with two different dosages (FIGS. 6A and 6B) of Ketoprofen Lysine co-crystal Form I (KL Co-xx), 1:1 admixture of Ketoprofen Lysine co-crystal Form I and Gabapentin (KL Co-xx-GAB MIX) or Gabapentin (GAB), compared to vehicle (rice starch) on mechanical allodynia measured as 50% withdrawal threshold (g), at 1, 3 and 6 hours after administration. All values represent mean±SEM in the individual groups. One-way ANOVA followed by Dunnett's test was applied for comparison between the vehicle control and compound-treated groups. Differences are considered significant at the p<0.05 level: * vs Vehicle, ° vs KL Co-xx, $ vs Gabapentin.
Figure 6B:
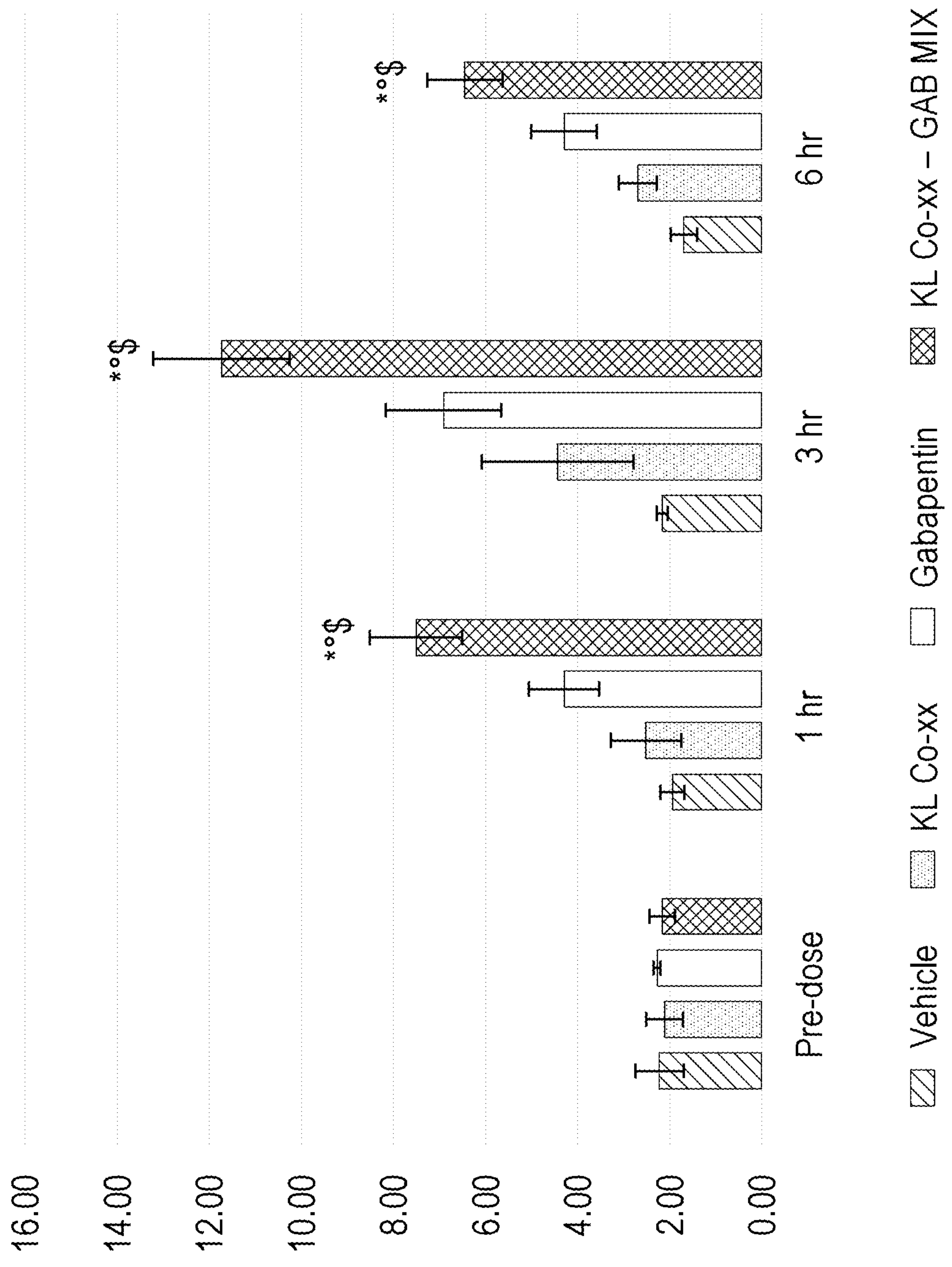

The results are shown in FIGS. 6A and 6B.

In particular, FIG. 6A shows the data from Ketoprofen Lysine co-crystal form I (KL Co-xx) [15.7 mg/kg, PO via capsule(s)], 1:1 admixture of Ketoprofen Lysine co-crystal form I and Gabapentin (KL Co-xx-GAB MIX) [15.7+6.8 mg/kg, PO via capsule(s)], Gabapentin [6.8 mg/kg, PO via capsule(s)] and vehicle (rice starch, PO via capsule) groups.

FIG. 6B shows the data from Ketoprofen Lysine co-crystal form I (KL Co-xx) [47.1 mg/kg, PC via capsule(s)], 1:1 admixture of Ketoprofen Lysine co-crystal form I and Gabapentin (KL Co-xx-GAB MIX) [47.1+20.4] mg/kg, PO via capsule(s)], Gabapentin [20.4 mg/kg, PO via capsule(s)], and vehicle (rice starch, PO via capsule) groups.

All values represent mean±standard error of the mean (SEM) in the individual groups. One-way ANOVA followed by Dunnett's test was applied for comparison between the vehicle control and compound-treated groups. Significance was considered at the $p<0.05$ level. The statistical analysis was performed by GraphPad Prism 5.0. Keys: *vs Vehicle, $ vs Gabapentin, ° vs Ketoprofen Lysine co-crystal.

From the graphs of FIGS. 6*a* and 6B appeared that the administration of the admixture of the invention (KL Co-xx-GAB MIX) significantly reduced the number of ipsilateral paw withdrawal in comparison with Ketoprofen Lysine co-crystal Form I and Gabapentin alone. Using the admixture of the invention (Ketoprofen Lysine co-crystal Form I and Gabapentin at 47.1+20.4 mg/kg), a statistically significant analgesic effect was observed at 1, 3 and 6 hours pot-dose.

Determination of Plasma and Brain Levels of Gabapentin and of the 1:1 Admixture of Gabapentin and Ketoprofen Lysine Co-Crystal Form I after Oral Administration as Capsules in the Rats The animals were housed in a single, exclusive room, air conditioned to provide a minimum of 15 air changes/hour. The environmental controls were set to maintain temperature within the range 22° C. and relative humidity within the range 50 to 60% with an approximate 12-hour light and 12-hour dark cycle that is controlled automatically. Food (Mucedola Standard GLP diet) and water were available ad libitum throughout the study. All animals were weighed on the day of each treatment.

Clinical signs were monitored at regular intervals throughout the study in order to assess any reaction to treatment. Each animal was uniquely identified with a coloured spray on the back before the experiment.

At the end of the study, animals were sacrificed by exsanguination under anesthesia.

The experiment was carried out in agreement with the Italian Law D. L.vo 4 marzo 2014, n. 26.

The experimental protocol consisted in blood and brain tissue sampling on the animals according to the following Tables 3 and 4 and in the analysis of the samples as described below.

TABLE 3

| Blood Sampling | |
|---|---|
| Animals/Time Point | 4/1 time point |
| Time points | 2 h |
| Fasting Requirements | Not required |
| Collection Site | Animals will be exsanguinated from caudal vein |
| Collection tube | Li heparin anticoagulant |
| Target Blood Volume | 70 μL |
| Sample Identification | Label indicating: Study number, animal ID, test item ID, sampling time |
| Sample Requirements | Stored in ice and centrifuged at +4° C., 3000 g for 10 minutes |
| Final Sample Storage Conditions | −20° C. until bioanalysis |

TABLE 4

| Brain tissue sampling | |
|---|---|
| Animals/Time Point | 4/1 time point |
| Time points | 2 hr |
| Fasting Requirements | Not required |
| Sample treatment | Brains are washed in saline, dried and weighted and place in tubes. |
| Sample Identification | Label indicating: Study number, animal ID, test item ID, sampling time |
| Sample Requirements | Stored in ice and centrifuged at +4° C., 3000 g for 10 minutes |
| Final Sample Storage Conditions | −20° C. until bioanalysis |

Aim of the study was the determination of the brain penetration of Gabapentin alone compared to the physical mixture of Gabapentin and Ketoprofen Lysine co-crystal Form I after administration in capsules in rats.

Sprague Dawley male rats (body weights 310 gr at the time of the treatment) were used in this study. The animals were originally supplied by Harlan, Italy. Once receipt from the supplier, the animals were subjected to health examinations and acceptance. The animals were housed, in a group of three, in cages suitable for the species and were routinely kept in the following environment except for short periods of time where experimental procedures dictated otherwise. The animals were acclimatized to local housing conditions for approximately 5 days.

Stock solutions of Ketoprofen Lysine co-crystal form I and Gabapentin were prepared at 1 mg/mL in MeOH and a mix stock solution was prepared by dilution of the two mentioned before to reach a final concentration of 100 μg/mL of each analyte. Stock solutions of DF1681Y and Gabapentin Impurity A were prepared respectively at 2 mg/mL and 1 mg/mL in MeOH. A mixture of the two was prepared in ACN with a final concentration of 5000 and 500 ng/mL respectively (mix IS).

Calibration curve and QC samples were prepared in rat blank plasma by adding 2 μL of each stock solution to 18 μL plasma. Spiked plasma samples were added to 200 μL of mix IS and centrifuged for 5 min at 9000g at 5° C. Samples from the oral treatments were prepared diluted 1:10 in blank plasma and 20 μL of the diluted plasma were processed as described above. 100 μL of extracted samples were then diluted 120 μL of mobile phase A.

Brain collected were homogenized in ammonium formiate 10 mM buffer 1 g/5 mL. Samples as well calibrants and QC samples were prepared by adding 20 μL of brain homogenate to 200 μL of mix IS and centrifuged for 5 min at 9000g at 5° C. 100 μL of extracted samples were then diluted 120 μL of mobile phase A.

Rat plasma levels of Gabapentin were measured after administration of two capsules of Gabapentin alone and of the 1:1 admixture of Ketoprofen Lysine co-crystal Form I and Gabapentin as a physical mixture. The percentage ratio of concentration of Gabapentin in brain vs plasma is reported in FIG. 7.

Figure 7:
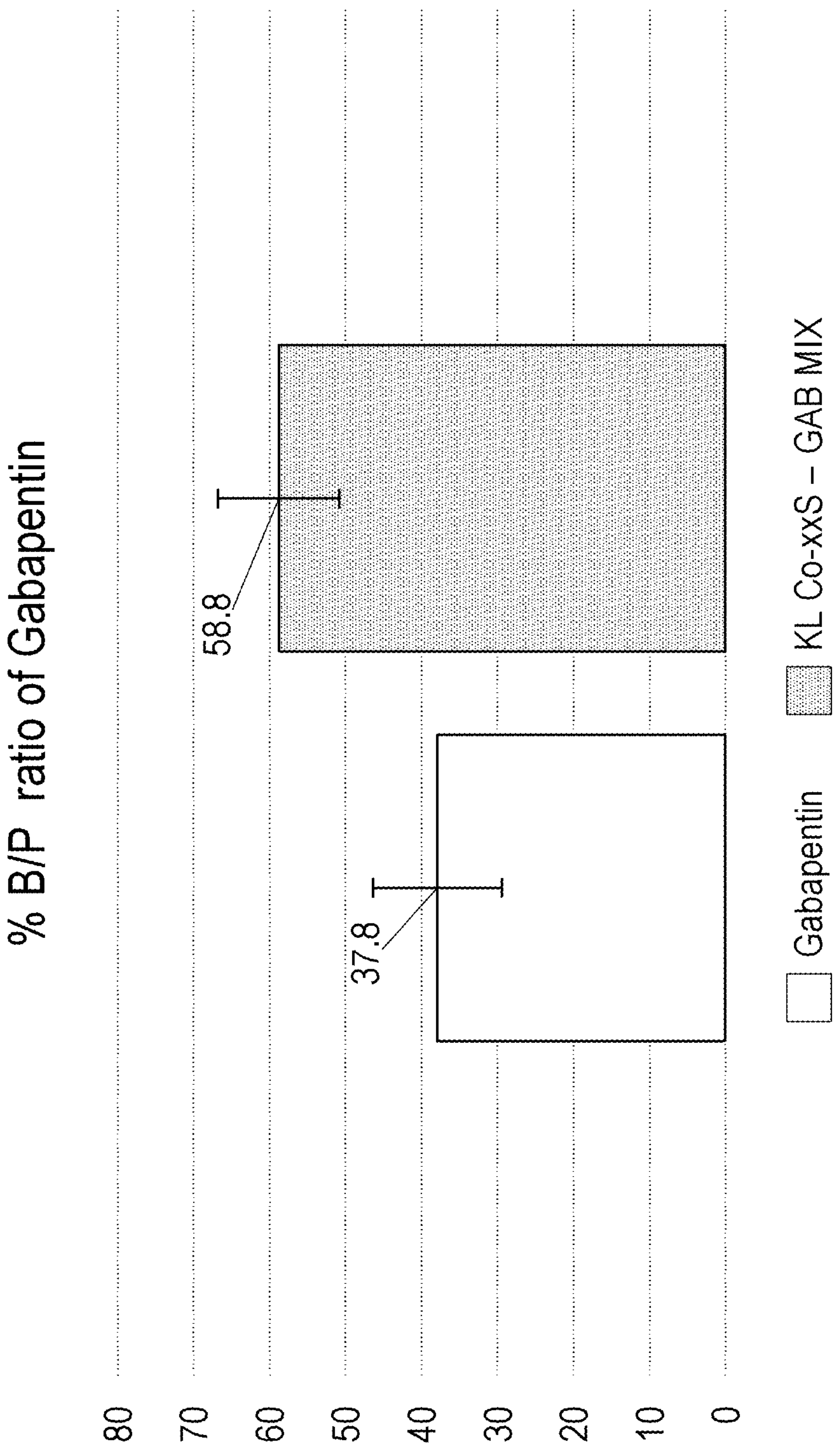
FIG. 7: bar chart of brain penetration ratio (brain I plasma %) of Gabapentin, when administrated orally, alone (Gabapentin) or as a 1:1 admixture with Ketoprofen Lysine co-crystal form I (KL Co-xx-GAB MIX).

Brain and plasma concentrations of the Gabapentin were assessed after 2 hours resulting in a brain/plasma penetration ratio of 37.8% for Gabapentin when administrated alone versus 58.8% when administrated as an admixture with Ketoprofen Lysine co-crystal form I (FIG. 7). Interestingly, the administration of Gabapentin in admixture with Ketoprofen Lysine co-crystal form I increased Gabapentin brain penetration compared to Gabapentin administered alone.

The invention claimed is:

1. A pharmaceutical composition comprising an admixture of synergistically effective molar ratios of Gabapentin and Ketoprofen, wherein the Ketoprofen is Ketoprofen Lysine co-crystal Form I characterized by an X-ray diffraction pattern with characteristic peaks at 16.3, 17.5, 17.6, 17.7, 19.6, and 19.7° 2theta ±0.20 degrees, and at least one pharmaceutically acceptable excipient, wherein the composition is an oral solid or liquid composition.

2. The admixture of claim 1, wherein the molar ratio of the components is comprised between 100:1 and 1:100.

3. The admixture of claim 2, wherein the molar ratio of the components is comprised between 50.1 and 1:50.

4. The admixture of claim 1, wherein the molar ratio of the components is comprised between 20:1 and 1:20.

5. The admixture of claim 4, wherein the molar ratio of the components is comprised between 10:1 and 1:10.

6. The admixture of claim 5, wherein the molar ratio of the components is comprised between 5:1 and 1:5.

7. The admixture of claim 6, wherein the molar ratio of the components is comprised between 2:1 and 1:2.

8. The admixture of claim 1, wherein the Ketoprofen is (S)-Ketoprofen.

9. The admixture of claim 1, wherein the Lysine is (S)-Lysine.

10. A method for the prevention, reduction or treatment of pain and/or inflammation in a subject in need thereof, comprising oral administration of the composition according to claim 1.

11. The method according to claim 10, wherein the pain is acute or chronic pain.

12. The method according to claim 10, wherein said pain is selected from headache, toothache, menstrual pain, muscle pain, neuropathic pain, pain associated to neuroinflammation, diabetic neuropathy, cancer pain, osteoarthritis, low back pain, sciatalgia, fibromyalgia, trigeminal neuralgia; post-surgical and post-operative pain, post herpetic neuralgia, rheumatoid arthritis, ankylosing spondylitis, frozen shoulder, phantom limb pain or HIV pain.

13. The pharmaceutical composition of claim 1, which contains 0.5-60% by weight of said admixture and 40-99.5% by weight of one or more pharmaceutically acceptable excipients.

14. A pharmaceutical composition comprising an admixture of Gabapentin and Ketoprofen, wherein the Ketoprofen is Ketoprofen Lysine co-crystal Form I characterized by an X-ray diffraction pattern with characteristic peaks at 16.3, 17.5, 17.6, 17.7, 19.6, and 19.7° 2theta ±0.20 degrees, and wherein the molar ratio of the Gabapentin and the Ketoprofen is 1:1, and at least one pharmaceutically acceptable excipient, wherein the composition is an oral solid or liquid composition.

* * * * *